United States Patent
Hoyme et al.

(10) Patent No.: US 11,027,138 B2
(45) Date of Patent: Jun. 8, 2021

(54) LOCATION-BASED SERVICES

(71) Applicant: Cardiac Pacemakers, Inc., St. Paul, MN (US)

(72) Inventors: Kenneth P. Hoyme, Plymouth, MN (US); James Kalgren, Lino Lakes, MN (US); John LaLonde, Lake Elmo, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 846 days.

(21) Appl. No.: 13/892,668

(22) Filed: May 13, 2013

(65) Prior Publication Data

US 2014/0058383 A1 Feb. 27, 2014

Related U.S. Application Data

(60) Provisional application No. 61/693,398, filed on Aug. 27, 2012.

(51) Int. Cl.
*A61N 1/372* (2006.01)

(52) U.S. Cl.
CPC ..... *A61N 1/37247* (2013.01); *A61N 1/37217* (2013.01)

(58) Field of Classification Search
CPC ............ A61N 1/37247; A61N 1/37217; A61N 1/37252
See application file for complete search history.

(56) References Cited

U.S. PATENT DOCUMENTS

| 5,488,410 | A | | 1/1996 | Lieberfarb et al. |
| 6,083,248 | A | | 7/2000 | Thompson |
| 6,154,673 | A | * | 11/2000 | Morgan ............... A61N 1/3993 607/5 |

(Continued)

FOREIGN PATENT DOCUMENTS

| CN | 104768608 | 7/2015 |
| EP | 2888001 | 9/2016 |

(Continued)

OTHER PUBLICATIONS

"Second Office Action," for Chinese Patent Application No. 201380044726.9 dated Sep. 27, 2016 (17 pages) with English translation.

(Continued)

*Primary Examiner* — Linda C Dvorak
*Assistant Examiner* — Ryan T Clark
(74) *Attorney, Agent, or Firm* — Pauly, DeVries Smith & Deffner LLC

(57) ABSTRACT

An apparatus comprises an external device for communication with an implantable device. The external device includes a communication circuit configured to receive a communication signal from at least one other device different from the implantable device, a locating circuit configured to determine a location of the external device using the received communication signal, and a control circuit electrically coupled to the communication circuit and the locating circuit. The control circuit is configured to determine whether the determined location imposes a limit on functionality of an implantable device, and provide user access to an implantable device feature according to the determined location.

10 Claims, 3 Drawing Sheets

(56) References Cited

U.S. PATENT DOCUMENTS

| | | |
|---|---|---|
| 6,386,882 B1 | 5/2002 | Linberg |
| 6,678,560 B1 | 1/2004 | Gilkerson et al. |
| 6,740,075 B2 | 5/2004 | Lebel et al. |
| 6,804,554 B2 | 10/2004 | Ujhelyi et al. |
| 6,810,290 B2 | 10/2004 | Lebel et al. |
| 7,043,305 B2 | 5/2006 | Kenknight et al. |
| 7,167,755 B2 | 1/2007 | Seeberger et al. |
| 7,270,633 B1 | 9/2007 | Goscha et al. |
| 7,273,457 B2 | 9/2007 | Penner |
| 7,565,197 B2 | 7/2009 | Haubrich et al. |
| 7,630,773 B2 | 12/2009 | Seeberger et al. |
| 7,641,619 B2 | 1/2010 | Penner |
| 7,805,199 B2 | 9/2010 | KenKnight et al. |
| 7,890,180 B2 | 2/2011 | Quiles |
| 9,031,652 B2 | 5/2015 | Hoyme et al. |
| 9,265,960 B2 | 2/2016 | Hoyme et al. |
| 2005/0204134 A1 | 9/2005 | Von Arx et al. |
| 2005/0288736 A1 | 12/2005 | Persen et al. |
| 2006/0074463 A1* | 4/2006 | Seeberger .......... A61N 1/37252 607/60 |
| 2006/0253301 A1 | 11/2006 | Simms et al. |
| 2006/0287693 A1 | 12/2006 | Kraft et al. |
| 2007/0288069 A1 | 12/2007 | Goscha et al. |
| 2008/0244717 A1 | 10/2008 | Jelatis et al. |
| 2009/0063187 A1* | 3/2009 | Johnson ............... A61B 5/0022 705/2 |
| 2009/0088820 A1* | 4/2009 | Mao .................... A61N 1/37264 607/59 |
| 2010/0049279 A1 | 2/2010 | Seeberger |
| 2011/0092799 A1* | 4/2011 | Steckner ............. A61N 1/3718 600/411 |
| 2011/0098788 A1 | 4/2011 | Quiles |
| 2011/0145588 A1 | 6/2011 | Stubbs et al. |
| 2011/0152970 A1* | 6/2011 | Jollota .................. H04W 4/005 607/60 |
| 2014/0058468 A1 | 2/2014 | Hoyme et al. |
| 2015/0190647 A1 | 7/2015 | Hoyme et al. |

FOREIGN PATENT DOCUMENTS

| | | |
|---|---|---|
| WO | 2012063154 | 5/2012 |
| WO | 2014035494 | 3/2014 |

OTHER PUBLICATIONS

"Communication under Rule 71(3) EPC," for European Patent Application No. 13728263.8 dated Apr. 8, 2016 (35 pages).

"First Office Action," for Chinese Patent Application No. 201380044726.9 dated Feb. 1, 2016 (20 pages) with English Translation.

"Communication Pursuant to Rules 161(1) and 162EPC," for European Patent Application No. 13728263.8, dated Jun. 8, 2015 (2 pages).

"International Preliminary Report on Patentability," for PCT/US2013/040736 related to co-pending U.S. Appl. No. 13/892,668, dated Mar. 3, 2015 (8 pages).

"International Search Report and Written Opinion," for PCT/US2013/040736 related to co-pending U.S. Appl. No. 13/892,668, dated Jan. 31, 2014 (13 pages).

"Response to Communication Pursuant to Rules 161 and 162 EPC," for European Patent Application No. 13728263.8, filed with the EPO on Oct. 1, 2015 (63 pages).

File History, for U.S. Appl. No. 13/892,632, filed May 13, 2013 to Apr. 22, 2015 (140 pages).

File History, for U.S. Appl. No. 14/661,511, filed Mar. 18, 2015 to Feb. 3, 2016 (166 pages).

* cited by examiner

LOCATION-BASED SERVICES

CLAIM OF PRIORITY

This application claims the benefit of priority under 35 U.S.C. § 119(e) of Hoyme et al., U.S. Provisional Patent Application Ser. No. 61/693,398, entitled "LOCATION-BASED SERVICES", filed on Aug. 27, 2012, which is herein incorporated by reference in its entirety.

BACKGROUND

Medical devices include devices designed to be implanted into a patient. Some examples of these implantable medical devices (IMDs) include cardiac function management (CFM) devices such as implantable pacemakers, implantable cardioverter defibrillators (ICDs), cardiac resynchronization therapy devices (CRTs), and devices that include a combination of such capabilities. The devices can be used to treat patients or subjects using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of IMDs include implantable diagnostic devices, implantable drug delivery systems, or implantable devices with neural stimulation capability.

IMDs can be sophisticated devices that can provide many advanced functions. External devices, such as IMD programmers, can communicate with an IMD using wireless telemetry and can be used to set device parameters. IMDs can also provide diagnostic data from one or more physiologic sensors. The programmers or other external devices IMDs can also be used to collect diagnostic data obtained by one or more physiologic sensors of the IMD. Programming IMDs has become more complicated as therapeutic and diagnostic features are added to these types of devices. Interfaces to interact with these devices can be difficult for someone who only occasionally has to access the device. Therefore, it is desirable to simplify interactions with these complicated devices.

Overview

This document relates generally to systems, devices, and methods for communication among an implantable device and external devices. An apparatus example includes an external device for communication with an implantable device. The external device includes a communication circuit configured to receive a communication signal from at least one other device different from the implantable device, a locating circuit configured to determine a location of the external device using the received communication signal, and a control circuit electrically coupled to the communication circuit and the locating circuit. The control circuit is configured to determine whether the determined location imposes a limit on functionality of an implantable device, and provide user access to an implantable device feature according to the determined location.

This section is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, the various examples discussed in the present document.

DETAILED DESCRIPTION

Figure 1:
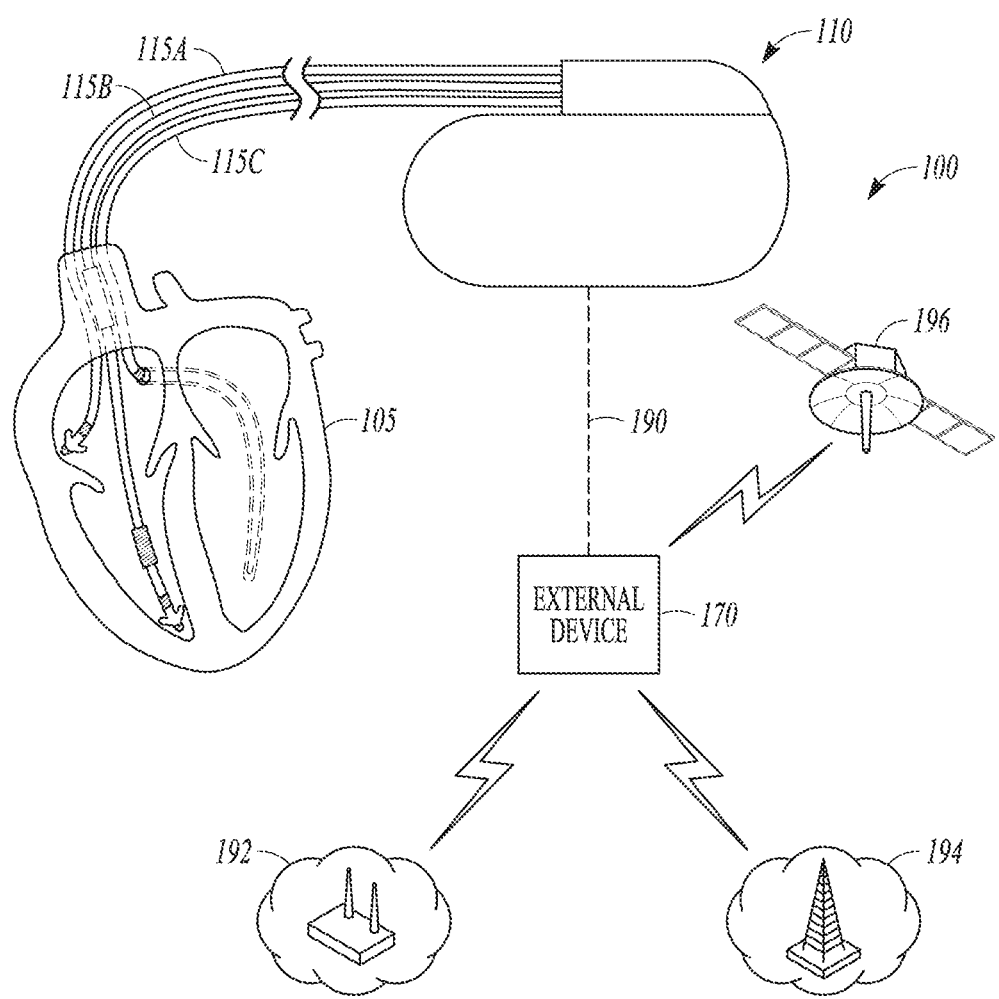
FIG. 1 is an illustration of an example of portions of a system that includes an IMD.

FIG. 1 is an illustration of an example of portions of a system that includes an IMD 110. Examples of IMD 110 include, without limitation, a pacemaker, a defibrillator, a cardiac resynchronization therapy (CRT) device, or a combination of such devices. The system 100 also typically includes an external device 170, such as an IMD programmer, that communicates wireless signals 190 with the IMD 110, such as by using radio frequency (RF) or other telemetry signals.

The IMD 110 can be coupled by one or more leads 115A-C to heart 105. Cardiac leads 115A-C include a proximal end that is coupled to IMD 110 and a distal end, coupled by electrical contacts or "electrodes" to one or more portions of a heart 105. The electrodes typically deliver cardioversion, defibrillation, pacing, or resynchronization therapy, or combinations thereof to at least one chamber of the heart 105. The electrodes may be electrically coupled to sense amplifiers to sense electrical cardiac signals. Sensed electrical cardiac signals can be sampled to create an electrogram. An electrogram can be analyzed by the IMD and/or can be stored in the IMD 110 and later communicated to the external device 170 where the sampled signals can be displayed for analysis.

As explained previously herein, programming of IMDs can be complicated and interfaces to interact with these devices can be difficult for someone who only occasionally has to access the device. The functions needed to be performed by an external device can be tied to location. Therefore, user interaction with the IMD can be simplified if the user interface only includes those functions tied to a given location.

Figure 2:
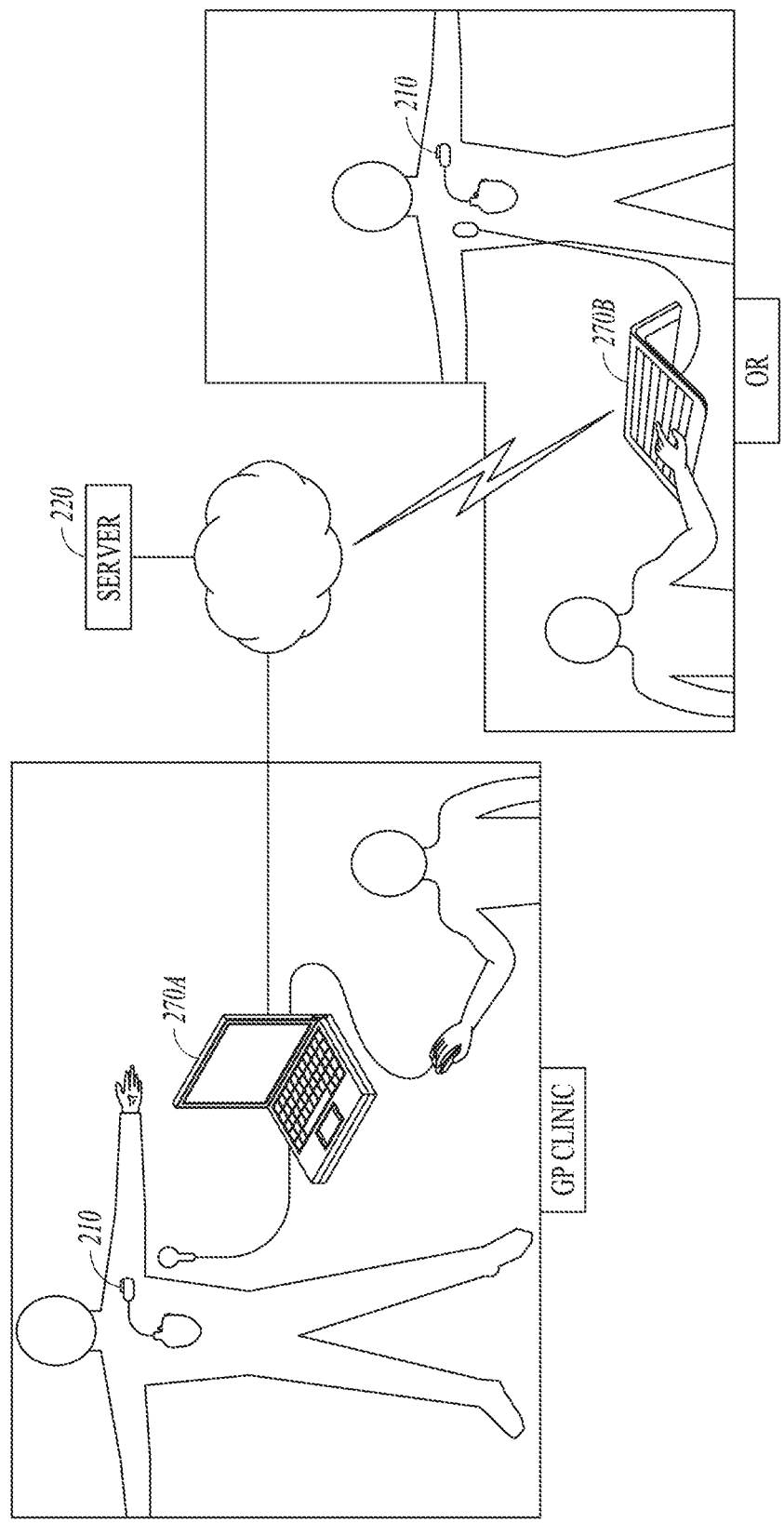
FIG. 2 is an illustration representing programming an IMD at different locations.

FIG. 2 is an illustration representing programming an IMD at different locations. One of the locations may be a general practice (GP) clinic. An external device 270A, 270B is used to program an IMD 210. Functionality at the general practice clinic may only require that certain information be read from the IMD 210 (e.g., for the physician or for uploading to one or more servers 220 remote from the general practice clinic), while functionality at a cardiologist's office may require full programming capability. The services required at the general practice clinic can be much more limited than the services required at the cardiologist's office and the user interface for the external device 270A, 270B can therefore be greatly simplified when the external device is located at the general practice clinic. In another example, the location is an operating room (OR). The IMD 210 may be an ICD. The required functionality of the user interface of the external device 270A, 270B may only be to turn defibrillation detection and therapy in the IMD 210 off and on.

It can be seen that the capabilities provided by the external device 270 can be changed based on the location of the device. If the external device 270A, 270B is able to determine its location, the user interface of the external device 270A, 270B can be automatically tailored and often simplified to meet the requirements of the location.

Figure 3:
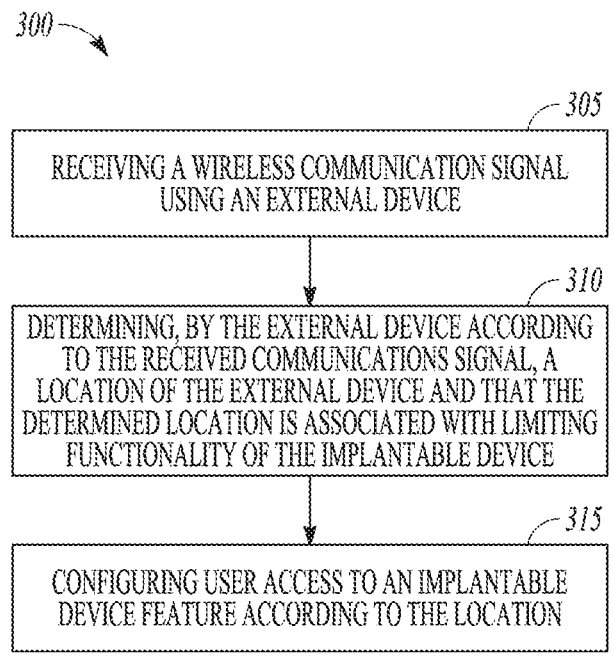
FIG. 3 is a flow diagram of an example of a method of providing location-based medical device services to a user.

FIG. 3 is a flow diagram of an example of a method 300 of providing location-based medical device services to a user. At block 305, a wireless communication signal is received using an external device. The external device can communicate with an implantable device (e.g., an IMD) and receive the wireless communication signal from at least one other device separate from the implantable device. As shown in FIG. 1, the wireless communication signal can be received from, among other things, a local area network (LAN) 192, a cellular telephone network 194, and a global positioning system (GPS) satellite 196. The wireless communication signal may be received using a communication circuit different from a telemetry circuit or telemetry system used for communication between the external device and the implantable device.

At block 310, the location of the external device is determined by the external device according to the received communication signal. The external device also determines whether the location is associated with limiting functionality of the implantable device. At block 315, user access to implantable device features is configured by the external device according to the determined location.

Figure 4:
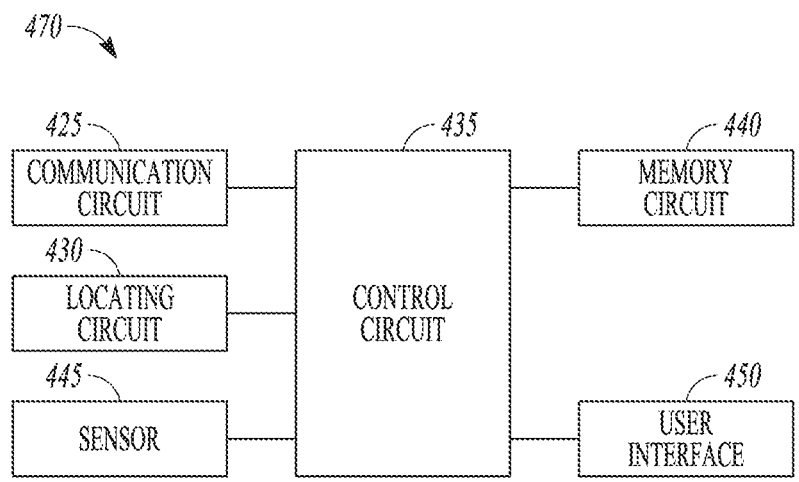
FIG. 4 is a block diagram of an example of portions of an external device for communication with an implantable device.

FIG. 4 is a block diagram of an example of portions of an external device 470 for communication with an implantable device. The external device 470 includes a communication circuit 425, a locating circuit 430, and a control circuit 435 that is electrically coupled to the communication circuit 425 and the locating circuit 430. In some examples, the communication circuit 425 includes a radio frequency (RF) receiver or transceiver. The communication circuit 425 receives a communication signal from at least one other device different from the implantable device, and the locating circuit 430 determines a location of the external device 470 using the received communication signal. The external device 470 may communicate with an implantable device using the communication circuit 425, or the external device 470 may include a separate telemetry circuit (not shown) for communication with the implantable device.

The control circuit 435 can include a microprocessor, a digital signal processor, application specific integrated circuit (ASIC), or other type of processor, interpreting or executing instructions in software modules or firmware modules. The control circuit 435 can include other circuits or sub-circuits to perform the functions described. These circuits may include software, hardware, firmware or any combination thereof. Multiple functions can be performed in one or more of the circuits or sub-circuits as desired.

The control circuit 435 determines whether the determined location imposes a limit on functionality of an implantable device and provides user access to one or more implantable device features according to the determined location. For example, the control circuit 435 may determine that the location of the external device is an OR, an emergency room (ER), a magnetic resonance imaging (MRI) clinic, a catheterization lab, a cardiology clinic, an electrophysiology clinic, a hospital, or a general practice clinic, and configure (e.g., selectively provide or limit) user access to implantable device features accordingly.

The locating circuit 430 can include one or more of software, firmware, and hardware to perform the functions described herein. In certain examples, the locating circuit 430 is integral to the control circuit 435. In some examples, a tablet computer or a cellular telephone is integrated into the external device 470, and the locating circuit 430 is included in the tablet computer or cellular telephone.

In some examples, the locating circuit 430 determines the location of the external device 470 using global positioning (e.g., GPS, or assisted GPS). The communication signal may include one or more messages transmitted from satellites and the locating circuit 430 may determine the location of the external device 470 using the satellite transmission.

The locating circuit 430 may cross reference coordinates determined by global positioning with map information to determine that the coordinates are related to a hospital location or to a type of clinic for example. The map information may be stored in a memory circuit 440 integral to, or electrically coupled to, the control circuit 435, or the map information may be stored in a remote server (e.g., a cloud server or cloud computer) accessed by the control circuit 435 using the communication circuit 425 or other port (e.g. a universal serial bus) to access the Internet.

In some examples, the locating circuit 430 determines the location of the external device 470 using cellular phone tower (e.g., cell site) information. The communication circuit 425 may receive a communication signal transmitted from a cell tower. The received communication signal may identify the cell tower transmitting the signal and the locating circuit 430 determines the location of the external device 470 from the cell tower identification. The locating circuit 430 may cross reference the cell tower information with location information (e.g., using a lookup table) from the memory or from access to cloud computing resources to determine the location of the external device 470.

In some examples, the locating circuit 430 determines the location of the external device 470 using wireless fidelity (WiFi) network mapping. The communication circuit 425 may receive a communication signal transmitted by a wireless fidelity (WiFi) network. The received communication signal may identify the WiFi network the locating circuit 430 may include a cross reference of WiFi nodes or networks for one or more areas. The received communication signal may identify the WiFi node or network (e.g., using an internet protocol address), and the location can then be determined from the cross reference. In certain examples, the communication signal identifies a LAN and the locating circuit 430 identifies the location of the external device 470 from the identification of the LAN.

In some examples, the locating circuit 430 uses a combination of two or more methods to identify the location of the external device. WiFi network or LAN information may provide intra-building information to the locating circuit 430. This information can help to further identify a function being performed at a location initially identified with GPS or cell tower information.

For instance, the communication circuit 425 may receive both a cell tower signal and a signal from a LAN network. The locating circuit 430 may identify a more general area using the cell tower signal (e.g., to identify that the external device is in a hospital) and identify a more specific area using the LAN signal (e.g., identify that the external device 470 is located in an operating theater or OR).

In some examples, when a location of the external device 470 is determined, the locating circuit 430 may identify a communication network associated with the determined location. The control circuit 435 may store an identifier for the communication network in the memory circuit in association with the determined location in the memory circuit 440. The locating circuit 430 can then deduce the location the next time an identifying signal is received from the communication network.

In some examples, the locating circuit 430 detects physical activity to determine if the location is changing or to adjust the location determination. The external device 470 may include an activity sensor 445 electrically coupled to the locating circuit. Some examples of an activity sensor include an accelerometer and a tilt switch. The locating circuit 430 estimates the location of the external device 470 according to the location determined using the received communication signal and subsequent motion sensed using the activity sensor. This may be useful to detect a change in the intra-building location of the external device 470.

As explained previously herein, the control circuit 435 configures user access to one or more implantable device features according to the determined location. The external device 470 may include a user interface 450 electrically coupled to the control circuit. The user interface 450 may include one or more of a display, a mouse, a keyboard, and a touch sensitive or multi-touch sensitive display screen.

Using the user interface 450, the control circuit 435 may present implantable device features as available to a user according to the determined location. For example, the features may be selectable via indications presented on one or more user interface menus. The control circuit 435 may exclude presentation by the user interface 450 of an implantable device feature limited by the determined location. Excluding a feature may include not presenting the feature on a displayed menu or ghosting the feature on the display to indicate that the feature is not available to the user.

For example, it may be desirable to suspend the delivery of defibrillation therapy to a patient who is in an ER of a hospital. In response to the locating circuit 430 determining that the location of the external device 470 is an ER, the control circuit 435 configures the user interface to allow the user to enable or disable delivery of defibrillation therapy by the implantable device. The control circuit 435 may also allow the user to change a tachyarrhythmia detection rate of the implantable device in order to make the implantable device less sensitive to detection of tachyarrhythmia.

In another example, it may be desirable to place the implantable device in an electrocautery mode when the patient is undergoing surgery. In electrocautery mode, defibrillation or cardioversion therapy is disabled if the implantable device is an ICD. If the implantable device provides pacing therapy, electrocautery mode may include providing asynchronous pacing. In asynchronous pacing, the pacing pulses are delivered according to a timer and not according to sensed cardiac events. This prevents non-cardiac events (e.g., the electrocautery) that may be sensed by the implantable device from influencing the therapy being provided. In response to the locating circuit 430 determining that the location of the external device 470 is an OR, the control circuit 435 allows a user to initiate the electrocautery mode in the implantable device. In certain examples, the control circuit 435 prevents access to implantable device features other than electrocautery mode when determining that the external device is in an ER. In certain examples, the control circuit 435 allows some information stored in the implantable device to be read or uploaded from the implantable device by the user.

In another example, it may be desirable to place the implantable device in an MRI mode when the patient is to undergo magnetic resonance imaging. Similar to the electrocautery mode, defibrillation or cardioversion therapy can be disabled in the MRI mode to avoid noise from the MRI causing false positive indications of the need for therapy. The MRI mode may also involve asynchronous pacing, and the asynchronous pacing may be delivered at a rate that is higher than a determined intrinsic rate. Pacing at a rate higher than the intrinsic rate prevents the implantable device from pacing into an intrinsic depolarization due to the presence of noise.

In response to the locating circuit 430 determining that the location of the external device 470 is an MRI clinic, the control circuit 435 configures the user interface 450 to allow a user to enable an MRI mode in the implantable device. In some examples, the control circuit 435 configures the user interface 450 to allow a user to initiate a device-automated pacing threshold test when it is determined that the external device 470 is located in an MRI clinic. In certain examples, the control circuit 435 does not allow user access to MRI mode or electrocautery mode, or these modes are disabled, unless the external device 470 is in an MRI clinic or OR, respectively.

For various locations, such as an OR, ER, or MRI clinic, it may be desirable to turn one or both of tachyarrhythmia detection and cardioversion/defibrillation therapy off. There is a concern that the user of the external device 470 may leave the detection or therapy turned off when the patient leaves the location. In some examples, the control circuit 435 provides, on the user interface, an indication or alert as a reminder to turn one or both of the cardioversion/defibrillation therapy and tachyarrhythmia detection back on.

In some examples, the control circuit 435 presents a first alert to a user that delivery of defibrillation therapy is disabled and initiates a timer in the external device 470. The timer may be a timer circuit integral to, or electrically coupled to, the control circuit 435. The control circuit 435 may generate a second alert, upon timeout of the timer, regarding the disabled defibrillation therapy or disabled tachyarrhythmia detection.

In some examples, in response to the locating circuit 430 determining that the location of the external device 470 is a general practice clinic, the control circuit 435 configures the user interface to allow user read-only access to at least a portion of data or other information stored in the implantable device.

The control circuit 435 may initiate an action by the external device, without participation by a user, upon determining the location of the external device. For instance, the control circuit 435 may initiate communication of information to a remote server in response to the locating circuit 430 determining a location of the external device. The information to be communicated can be selected according to the determined location. In some examples, the remote server to receive the information is identified according to the determined location. For instance, the determined location may be a major medical center (e.g., Mayo Clinic). The control circuit 435 may initiate a transfer of information to a remote server associated with the medical center in response to determining that the external device 470 is located at the medical center. The selected information may be communicated to the remote server absent participation or prompting by a user. This allows specified information to be made readily accessible to those people with the appropriate training. In some examples, emergency information can be transferred to a remote server and actions to address the emergency can be automatically dispatched.

The selected information may include location information and identification information of the external device. In this way, a field clinical engineer (FCE) or other device expert may be able to determine the locations of all units on a given site (e.g., a hospital). This information may be relayed to a handheld device (e.g., a smart phone) of the FCE. Alerts from external devices may also be relayed to such handheld devices.

For some locations, the control circuit 435 allows user access to substantially all of the features of the implantable medical device. For instance, if the locating circuit 430 determines that the external device is located in the office of a cardiologist, a cardiology clinic, or an electrophysiology clinic, the control circuit 435 may allow user access to all programmable device parameters. Some device capability, such as changing executable code in the implantable device may still not be allowed by the control circuit 435.

Other levels of functionality may be desired for other locations. For instance, if the locating circuit 430 determines that the external device is located in a catheterization lab, the control circuit 435 may turn cardioversion or defibrillation therapy off and allow user access to pacing therapy capture detection tests.

In some examples, the control circuit 435 presents the user interface in a language appropriate to the detected location. For example, certain languages or language dialects can be associated with particular locations. The control circuit 435 may display user options in the language specified for the determined location.

In some examples, the external device 470 is dedicated to a certain location. In other words, it is intended that the external device 470 only be used at a specified location. When the locating circuit 435 determines that the location of the external device 470 is not at the specified location, the control circuit 435 may disable the external device 470 altogether (e.g., "brick" the device).

It can be seen from the examples described herein that because functions required to be performed by an external device are often dependent upon location, determining the location with the external device can lead to simplification of user interaction with an implantable device.

Additional Notes and Examples

Example 1 includes subject matter (such as an apparatus or device) comprising an external device for communication with an implantable device. The external device comprises a communication circuit configured to receive a communication signal from at least one other device different from the implantable device, a locating circuit configured to determine a location of the external device using the received communication signal, and a control circuit electrically coupled to the communication circuit and the locating circuit. The control circuit is configured to: determine whether the determined location imposes a limit on functionality of an implantable device, and provide user access to an implantable device feature according to the determined location.

In Example 2, the subject matter of Example 1 optionally includes a control circuit configured to determine that the location of the external device is at least one of an operating room (OR), an emergency room (ER), a magnetic resonance imaging (MRI) clinic, a catheterization laboratory, a cardiology clinic, an electrophysiology clinic, a hospital, and a general practice clinic.

In Example 3, the subject matter of one or any combination of Examples 1 and 2 optionally includes a locating circuit configured to determine the location of the external device using at least one of global positioning, wireless fidelity (WiFi) network mapping, cellular telephone tower identification, and local area network (LAN) identification.

In Example 4, the subject matter of one or any combination of Examples 1-3 optionally includes an activity sensor electrically coupled to the locating circuit. The locating circuit is optionally configured to estimate the location of the external device according to the location determined using the received communication signal and subsequent motion sensed using the activity sensor.

In Example 5, the subject matter of one or any combination of Examples 1-4 optionally includes a user interface electrically coupled to the control circuit. The control circuit is optionally configured to: present, using the user interface, the implantable device feature as available to a user according to the determined location, and exclude presentation by the user interface of an implantable device feature limited by the determined location.

In Example 6, the subject matter of Example 5 optionally includes a control circuit configured to allow, in response to the locating circuit determining that the location of the external device is an ER and via the user interface, a user to at least one of: enable or disable delivery of defibrillation therapy by the implantable device, and change a tachyarrhythmia detection rate of the implantable device.

In Example 7, the subject matter of one or any combination of Examples 5 and 6 optionally includes a control circuit configured to allow, via the user interface and in response to the locating circuit determining that the location of the external device is an OR, a user to initiate an electrocautery mode in the implantable device in which defibrillation therapy is disabled. When the electrocautery mode is initiated by a user, the control circuit is optionally configured to: present a first alert to a user that delivery of defibrillation therapy is disabled, initiate a timer in the external device, and generate a second alert, upon timeout of the timer, regarding the disabled defibrillation therapy.

In Example 8, the subject matter of one or any combination of Examples 5-7 optionally includes a control circuit configured to allow, via the user interface and in response to the locating circuit determining that the location of the external device is an MRI clinic, a user to at least one of: enable an MRI mode in which cardiac pacing pulses are delivered asynchronously and at a rate higher than a determined intrinsic rate, and initiate a device-automated pacing threshold test.

In Example 9, the subject matter of one or any combination of Examples 5-8 optionally includes a control circuit configured to allow, via the user interface and in response to the locating circuit determining that the location of the external device is a general practice clinic, user read-access to at least a portion of information stored in the implantable device.

In Example 10, the subject matter of one or any combination of Examples 5-9 optionally includes a control circuit configured to display the user interface in a language specified for the determined location.

In Example 11, the subject matter of one or any combination of Examples 1-10 optionally includes a memory circuit integral to or electrically coupled to the control circuit. The locating circuit is optionally configured to identify a communication network associated with the determined location, and the control circuit is optionally configured to store an identifier for the communication network in the memory circuit in association with the determined location.

In Example 12, the subject matter of one or any combination of Examples 1-11 optionally includes a control circuit configured to: selectively load information stored in the implantable device according to the determined location, identify a remote server according to the determined location, and communicate the information to the remote server absent participation by a user.

Example 13, can include subject matter (such as a method, a means for performing acts, or a machine-readable medium including instructions that, when performed by the machine, cause the machine to perform acts), or can optionally be combined with the subject matter of one or any combination of Examples 1-10 to include such subject matter, comprising receiving a wireless communication signal using an external device, wherein the external device is configured to communicate with an implantable device and receive the wireless communication signal from at least one other device; determining, by the external device according to the received communication signal, a location of the external device and that the determined location is associated with limiting functionality of the implantable device; and configuring, by the external device, user access to an implantable device feature according to the determined location.

Such subject matter can include means for receiving a wireless communication signal using an external device, an illustrative example of which include a communication circuit configured to communicate wirelessly with one or more of a LAN, a cellular telephone network, a GPS, or a proprietary medical device telemetry system or circuit. Such subject matter can include means for determining, by the external device according to the received communication signal, a location of the external device and that the determined location is associated with limiting functionality of the implantable device, an illustrative example of which is a locating circuit included in the external device. Such subject matter can include means for configuring, by the external device, user access to an implantable device feature according to the determined location, an illustrative example of which is a control circuit included in the external device.

In Example 14, the subject matter of Example 13 can optionally include the external device determining that the location is at least one of an operating room (OR), an emergency room (ER), a magnetic resonance imaging (MRI) clinic, a catheterization laboratory, a cardiology clinic, an electrophysiology clinic, a hospital, and a general practice clinic.

In Example 15, the subject matter of one or any combination of Examples 13 and 14 optionally includes the external device determining the location using at least one of a global positioning system (GPS), wireless fidelity (WiFi) network mapping, cellular telephone tower identification, and local area network (LAN) identification.

In Example 16, the subject matter of one or any combination of Examples 13-16 optionally includes the external device determining that the location is a location where defibrillation therapy should be turned off in the implantable device and, in response to the determination, enabling user access for at least one of: disabling delivery of defibrillation therapy by the implantable device, and presenting a reminder to enable defibrillation therapy when the defibrillation therapy is disabled.

In Example 17, the subject matter of one or any combination of Examples 13-16 optionally includes the external device determining that the location is an OR and enabling user access for initiating an electrocautery mode in the implantable device in response to the determination.

In Example 18, the subject matter of one or any combination of Examples 13-17 optionally includes the external device determining that the location is an MRI clinic, and the external device enabling, in response to the determination, at least one of: user access to enable an MRI mode in which pacing therapy is delivered asynchronously at a rate higher than a determined intrinsic rate, and user access to enable a device-automated pacing threshold test.

In Example 19, the subject matter of one or any combination of Examples 13-18 optionally includes the external device determining that the location is a general practice clinic, and, in response to the determination, enabling user read-access to at least a portion of data stored in the implantable device.

In Example 20, the subject matter of one or any combination of Examples 13-19 optionally includes selectively loading, by the external device, information stored in the implantable device according to the determined location, identifying a remote server according to the determined location, and communicating the information to the remote server absent participation by a user.

Example 21 can include, or can optionally be combined with any portion or combination of any portions of any one or more of Examples 1-20 to include, subject matter that can include means for performing any one or more of the functions of Examples 1-20, or a machine-readable medium including instructions that, when performed by a machine, cause the machine to perform any one or more of the functions of Examples 1-20.

Each of these non-limiting examples can stand on its own, or can be combined in various permutations or combinations with one or more of the other examples.

The above detailed description includes references to the accompanying drawings, which form a part of the detailed description. The drawings show, by way of illustration, specific embodiments in which the invention can be practiced. These embodiments are also referred to herein as "examples." All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code can form portions of computer program products. Further, the code can be tangibly stored on one or more volatile or non-volatile computer-readable media during execution or at other times. These computer-readable media can include, but are not limited to, hard disks, removable magnetic disks, removable optical disks (e.g., compact disks and digital video disks), magnetic cassettes, memory cards or sticks, random access memories (RAM's), read only memories (ROM's), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

The claimed invention is:

1. An external device for communication with an implantable device, the external device comprising:
   a communication circuit configured to receive a communication signal from at least one other device different from the implantable device, wherein the communication circuit is configured to receive a first communication signal, a second communication signal, and a third communication signal;
   a locating circuit configured to determine a location of the external device using the received communication signals;
   a control circuit electrically coupled to the communication circuit and the locating circuit,
      in response to receiving the first communication signal, the locating circuit configured to determine that the location is a first location;
      in response to receiving the second communication signal, the locating circuit configured to determine that the location is an operating room, an emergency room, or a magnetic resonance imaging (MRI) clinic;
      in response to receiving the third communication signal, the locating circuit configured to determine that the location is a general practice clinic;
      in response to the locating circuit determining that the location is the general practice clinic, the control circuit configured to provide read-only access to the implantable device;
      in response to the locating circuit determining that the location is the operating room, the emergency room, or the MRI clinic, the control circuit configured to provide access to turn at least one of tachyarrhythmia detection and cardioversion/defibrillation therapy on and off; and
      in response to the locating circuit determining that the location is the first location, the control circuit configured to provide access to all programmable device parameters;
   wherein the first location is at least one of
      a cardiology clinic, and
      an electrophysiology clinic.

2. The external device of claim 1, wherein the locating circuit is configured to determine the location of the external device using at least one of global positioning, wireless fidelity (WiFi) network mapping, cellular telephone tower identification, and local area network (LAN) identification.

3. The external device of claim 2, including:
   an activity sensor electrically coupled to the locating circuit,
   wherein the locating circuit is configured to estimate the location of the external device according to the location determined using the received communication signal and subsequent motion sensed using the activity sensor.

4. The external device of claim 1, including a user interface electrically coupled to the control circuit, wherein the control circuit is configured to:
   present, using the user interface, one or more implantable device features as available to a user according to the programming of the implantable device functionality required by the determined location; and
   exclude presentation by the user interface of the one or more implantable device features limited by the programming of the implantable device functionality required by the determined location.

5. The external device of claim 4, wherein in response to the locating circuit determining that the location of the external device is an ER, the control circuit is configured to allow, via the user interface, the user to at least one of:
   enable or disable delivery of defibrillation therapy by the implantable device; and
   change a tachyarrhythmia detection rate of the implantable device.

6. The external device of claim 4,
   wherein in response to the locating circuit determining that the location of the external device is an OR, the control circuit is configured to allow, via the user interface, the user to initiate an electrocautery mode in the implantable device, wherein defibrillation therapy is disabled in the electrocautery mode, and
   wherein, when the electrocautery mode is initiated by a user, the control circuit is configured to:
      present a first alert to the user that delivery of defibrillation therapy is disabled,
      initiate a timer in the external device; and
      generate a second alert, upon timeout of the timer, regarding the disabled defibrillation therapy.

7. The external device of claim 4, wherein in response to the locating circuit determining that the location of the external device is an MRI clinic, the control circuit is configured to allow, via the user interface, the user to at least one of:

enable an MRI mode in which cardiac pacing pulses are delivered asynchronously and at a rate higher than a determined intrinsic rate; and initiate a device-automated pacing threshold test.

8. The external device of claim 4, wherein the control circuit is configured to present user options on the user interface in a language specified for the determined location.

9. The external device of claim 1, including:
a memory circuit integral to or electrically coupled to the control circuit,
wherein the locating circuit is configured to identify a communication network associated with the determined location, and
wherein the control circuit is configured to store an identifier for the communication network in the memory circuit in association with the determined location.

10. The external device of claim 1, wherein the control circuit is configured to:
selectively load information stored in the implantable device according to the determined location;
identify a remote server according to the determined location; and
communicate the information to the remote server absent participation by a user.

* * * * *